United States Patent
Park et al.

(10) Patent No.: US 9,808,273 B2
(45) Date of Patent: Nov. 7, 2017

(54) CUTTING APPARATUS OF A CUTTING SYSTEM USING A ROBOT

(71) Applicant: CUREXO, Inc., Seoul (KR)

(72) Inventors: Young-bae Park, Cheongju-si (KR); Chang-hun Song, Goyang-si (KR); Jae-jun Lee, Suwon-si (KR)

(73) Assignee: CUREXO, INC, Seoul (KR)

( * ) Notice: Subject to any disclaimer, the term of this patent is extended or adjusted under 35 U.S.C. 154(b) by 396 days.

(21) Appl. No.: 14/694,127

(22) Filed: Apr. 23, 2015

(65) Prior Publication Data

US 2015/0305766 A1  Oct. 29, 2015

(30) Foreign Application Priority Data

Apr. 24, 2014  (KR) ......................... 10-2014-0049307

(51) Int. Cl.
 *A61B 17/32* (2006.01)
 *A61B 17/16* (2006.01)
 *A61B 34/30* (2016.01)

(52) U.S. Cl.
 CPC .. *A61B 17/320016* (2013.01); *A61B 17/1633* (2013.01); *A61B 34/30* (2016.02)

(58) Field of Classification Search
 CPC ........ A61B 17/320016; A61B 17/1633; A61B 34/30
 See application file for complete search history.

(56) References Cited

U.S. PATENT DOCUMENTS

| | | | | |
|---|---|---|---|---|
| 5,026,376 A | * | 6/1991 | Greenberg | A61B 17/02 606/104 |
| 5,053,035 A | * | 10/1991 | McLaren | A61B 17/7208 606/62 |
| 5,494,359 A | * | 2/1996 | Del Rio | A61B 17/1633 384/518 |
| 5,784,542 A | * | 7/1998 | Ohm | B25J 3/04 700/247 |
| 6,209,886 B1 | * | 4/2001 | Estes | A61B 17/162 279/143 |

FOREIGN PATENT DOCUMENTS

| | | |
|---|---|---|
| JP | 9-56708 | 3/1997 |
| KR | 10-0873014 | 12/2008 |

* cited by examiner

*Primary Examiner* — Christian Sevilla
(74) *Attorney, Agent, or Firm* — Kile Park Reed & Houtteman PLLC (57) ABSTRACT

The present invention aims to provide a cutting apparatus of a cutting system using a robot for reducing the damage and interference of a bone, a muscle and a surrounding soft tissue on operating and improving durability by minimizing the diameter of the sleeve while improving the rigidity against the bending and not generating the chattering of the shaft.

8 Claims, 9 Drawing Sheets

CUTTING APPARATUS OF A CUTTING SYSTEM USING A ROBOT

BACKGROUND

Field

The present invention relates to a cutting apparatus of a cutting system using a robot, and more particularly, a cutting apparatus of a cutting system using a robot which prevents chattering of the shaft and minimizes the diameter of a sleeve while increasing the rigidity against bending of the sleeve, thereby being capable of reducing the damage and interference of a bone, a muscle and surrounding soft tissue during surgery, and improving the durability.

Description of the Related Art

Generally, in case the joint disease is in the early stage or is slight, the disease can be treated with non-surgical treatment such as a medicine treatment and a physical treatment. However, in case the joint disease is severe or it is impossible to live on a daily routine, it should be treated with a surgical treatment.

The surgical treatment may comprise arthroendoscopic surgical operation, autologous chondrocyte implantation, etc., and in case of a severe disease, an artificial joint surgery is performed. The artificial joint surgery is representatively performed by a human and a robot.

The artificial joint surgery using a robot is the surgical procedure of cutting knee bone and implanting the artificial knee joint (implant a of FIG. 1B) by rotating a cutter of a cutting apparatus provided in an end part of the flexible arm of the robot according to the information input into a computer.

Figure 1A:
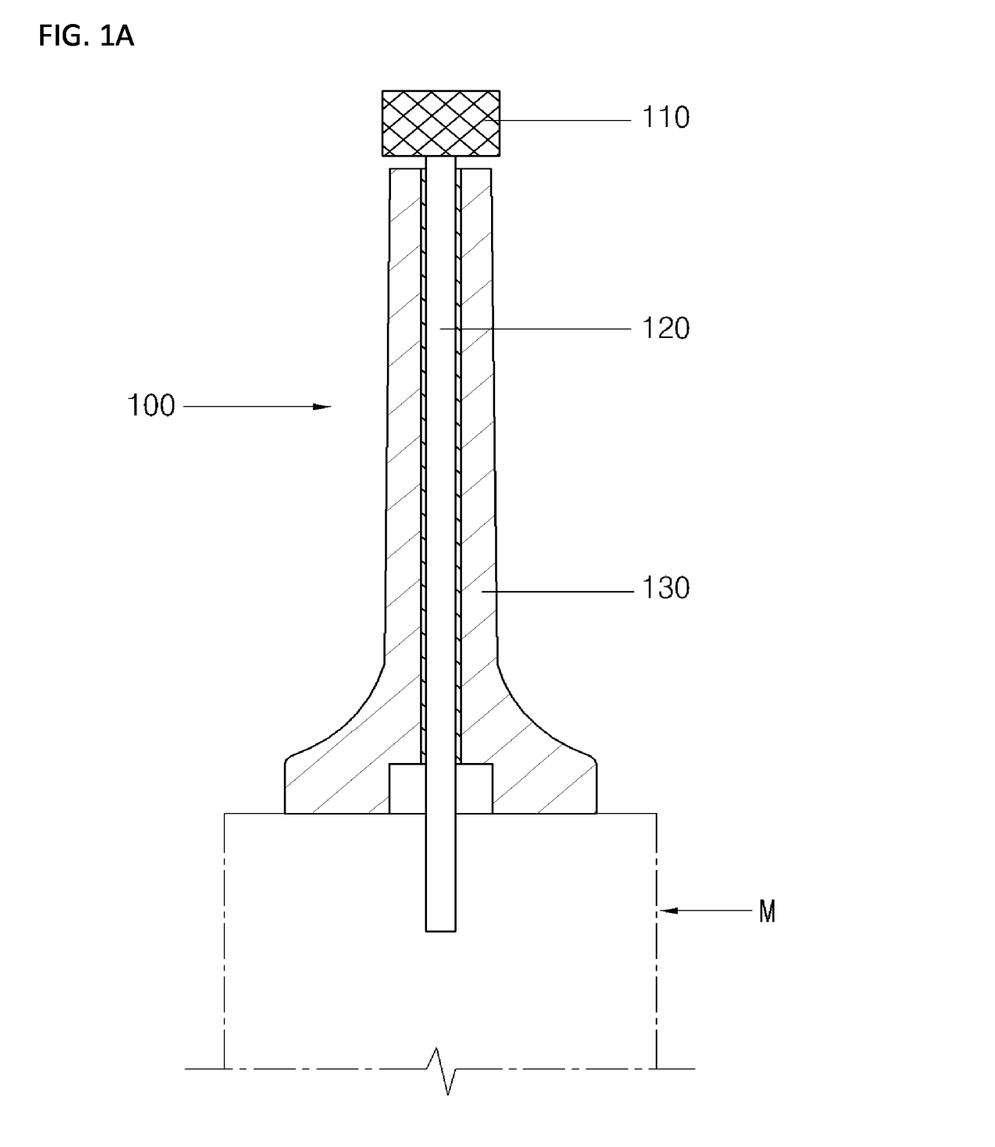
FIG. 1A is a drawing of a conventional cutting apparatus of a joint cutting system using a robot.
Figure 1B:
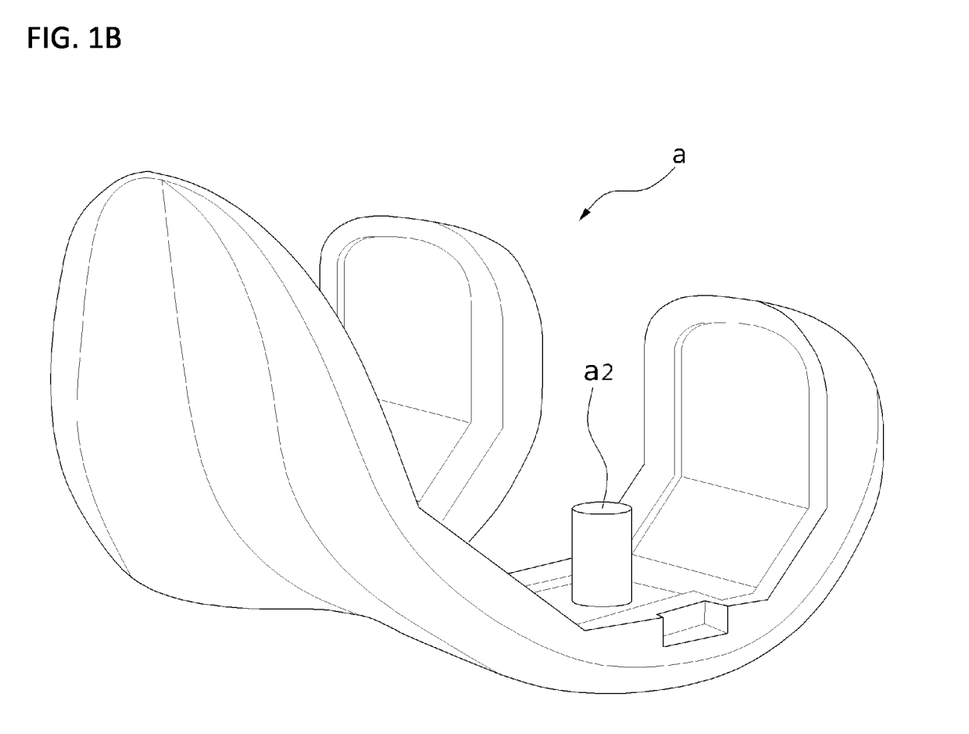
FIG. 1B is a schematic perspective view of an embodiment of an artificial joint (implant) operated on the knee joint.
Figure 2:
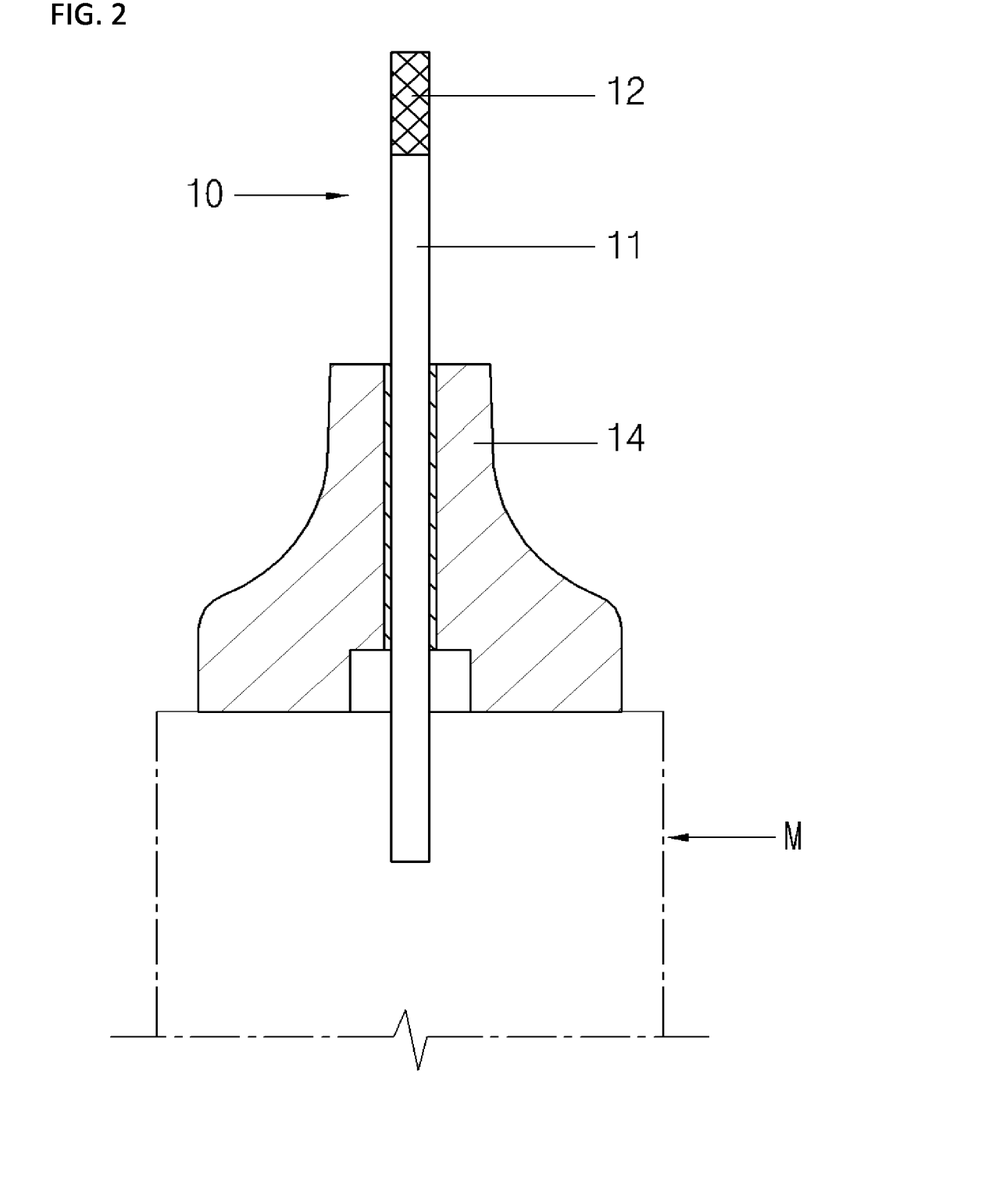
FIG. 2 is a drawing of another embodiment of a conventional cutting apparatus of a joint cutting system using a robot.

FIG. 1A is a drawing of a conventional cutting apparatus of a joint cutting system using a robot, and FIG. 1B is a schematic perspective view of an embodiment of an artificial joint (implant) operated on the knee joint. As shown in FIG. 1 and FIG. 2, the conventional cutting apparatus comprises a head 110 having a diameter of 7.8 mm and a shaft 120 having a diameter of 2.3 mm. The head 110 is installed on the end portion of the flexible arm of the robot and is equipped with a cutting blade at outer portion and front end portion of the head 110. The rear end portion of the shaft 120 is coupled with a motor M installed on the front portion of the flexible arm of the robot.

And the outer portion of the shaft 120 is supported by a sleeve 130 fixed to a housing of the motor M in order to be rotatable. Therefore, when the shaft 120 rotates, chattering or bending of the shaft 120 are not generated. Also, the head 110 protruded over the sleeve 130 performs cutting of bone while rotating.

The shaft 120 of the cutting apparatus shown in FIG. 1 as described above is inserted into a long sleeve 130 and then rotates. Therefore, since severe friction is generated, there are limitations that in use of long time the abrasion of the shaft 120 may occur and the shaft 120 may not rotate smoothly.

FIG. 2 is a drawing of another embodiment of a conventional cutting apparatus of a joint cutting system using a robot, and shows the cutting system using a robot disclosed in Korean Patent Registration No. 10-0873014.

Referring to FIG. 2, the joint cutting system using the robot includes a flexible arm and a motor M provided on the front end portion of the arm, wherein the sleeve 14 is coupled to the housing of the motor and the cutter 10 coupled to the axis of the motor is rotatably coupled into the sleeve 14. The cutter 10 has a round-bar shape and is coupled in order to rotate within the sleeve 14 by the motor.

And the system includes the shaft 11 having cantilever shape of being extended outside the sleeve 14, and the head 12 provided on the front end portion of the shaft extended outside the sleeve 14. The head 12 enters inside the bone like entering inside a tunnel while cutting the bone. For doing this, the length of the cantilever of the shaft 11 and the diameter of the head may be respectively 20~30 mm and 1.5~4.0 mm, or 70~80 mm and 4.0~6.0 mm.

Because the cutting apparatus shown in FIG. 2 as described above operates on the knee joint with tunnel-like cutting techniques using the cutter of cantilever shape with the minimum diameter and the maximum length optimized according to the diameter, the bone can be cut quickly and safely, and the damage of muscles or surrounding soft tissue attached to the bone can be reduced to some extent. However, there are disadvantages that because the shaft 11 is not supported by the sleeve 14 so as to be exposed as cantilever shape, bending and chattering of the shaft 11 are generated. In particular, considering that upon operating, the shaft 11 rotates at a speed of more than 60,000 rpm, there is disadvantage of lowering the safety, for example, a risk of breakdown of the shaft 11. In addition, considering the chattering of the shaft 11, there is limitation of the length of being exposed as the shape of the cantilever. Therefore, there is problem that the shaft 11 cannot be used at all in case the operative position is deep.

Recently, in order to compensate the disadvantages of FIGS. 1A and 2 as described above, the damage and interference of the bone, the muscle and the surrounding soft tissue was minimized by reducing the diameter of the sleeve. In addition, the cutter support member equipped with a plurality of bearings within the sleeve has been developed. (not shown)

However, in this type of cutter support member, bearings have to be inserted inside the sleeve of pipe-shape, and because the diameter of the sleeve must increase in order to meet the rigidity against bending, there is disadvantage that the overall outer diameter increases excessively. This increase of outer diameter of the sleeve causes the damage and the interference of a bone, a muscle and the surrounding soft tissue during operation.

SUMMARY

The present invention aims to provide a cutting apparatus of a cutting system using a robot for reducing the damage and interference of a bone, a muscle and a surrounding soft tissue on operating and improving durability by minimizing the diameter of the sleeve while improving the rigidity against the bending and not generating the chattering of the shaft.

In order to achieve the above object, a cutting apparatus of a cutting system using a robot according to the present invention comprises, a shaft coupled to a motor provided in an arm of a robot; a cutter equipped with a cutting head at an end of the shaft; and a sleeve into which the shaft is inserted, wherein, the sleeve comprises, a shaft insertion unit which is provided with a shaft insertion hole formed to insert the shaft; and a reinforcing wing unit formed to be extended integrally along with one side of the shaft insertion unit, thereby reinforcing rigidity against the bending of the shaft insertion unit.

The cutting apparatus may further comprise a plurality of support bearings installed inside the shaft insertion hole in order to support the shaft rotatably.

And the reinforcing wing unit may consist of support sections connected to both end regions of the shaft insertion unit and the regions into which the support bearings are inserted, and connecting sections for connecting the support sections, wherein hollow sections are formed between the support sections and the connecting sections.

In addition, the reinforcing wing unit may comprise a fixed wing section integrally connected to the shaft insertion unit and being rotatable, and a rotatable wing section connected to the fixed wing section and being rotatable.

Meanwhile, the cutting apparatus according to the present invention may comprise a plurality of first hinge sections which are installed on the fixed wing section and have pinholes perforating on the first hinge sections, a plurality of second hinge sections which are installed on the rotatable wing section in order to be connected to the first hinge sections and have pinholes perforating on the second hinge sections, and hinge pins inserted into the pinholes of the first hinge sections and the second hinge sections.

Meanwhile, the sleeve may be produced separately to a upper sleeve and a lower sleeve and then is assembled, and the upper sleeve and the lower sleeve comprise respectively a shaft groove and a washing water groove, wherein the shaft groove of the upper sleeve and the shaft groove of the lower sleeve are connected to form the shaft insertion hole, and the washing water groove of the upper sleeve and the washing water groove of the lower sleeve are connected to form the washing water supply hole.

By a cutting apparatus of a cutting system using a robot according to an embodiment of the present invention, although during operating, heavy load is generated by on the vertical and horizontal movement of the cutting head and the heavy load is applied to the shaft so that a bending load is repeatedly applied to a shaft insertion unit of a sleeve, a reinforcing wing unit reinforces the rigidity against the bending. Therefore, even if the overall thickness of the sleeve is minimized, the sleeve is not likely to bend or be deformed easily. Like this, because it is possible to reduce the damage and interference of a bone, a muscle and a surrounding soft tissue during operating while minimizing the thickness of the sleeve, there is an effect that it is possible to improve the safety of operation and shorten the recovery period of the patent.

In addition, by a cutting apparatus of a cutting system using a robot according to another embodiment of the present invention, when the cutting head moves on inclined surface or curved surface on cutting a bone, the reinforcing wing unit has structure which allows the cutting head to move angularly. Therefore, there is an effect that the cutting head can move smoothly without causing damage of body tissue, thereby improving the safety of convenience of the surgery and shortening the surgery time.

1: cutter
11: shaft
12: cutting head
2: sleeve
2a: upper sleeve
2b: lower sleeve
21: shaft insertion section
22: reinforcing wing section
22a: support section
22b: connection section
22c: hollow section
23: shaft insertion hole
23a,23b: shaft groove
221: fixed wing section
222: rotatable wing section
223: first hinge section
224: second hinge section
225: hinge pin
24: washing water supply hole
24a,24b: washing water groove
25: bearing insertion groove
4: support bearing
41: first support bearing
42: second support bearing
43: third support bearing

DETAILED DESCRIPTION OF EXEMPLARY EMBODIMENTS

Hereinafter, an embodiment of the present invention would be explained in detail referring to appended drawings.

Figure 3:
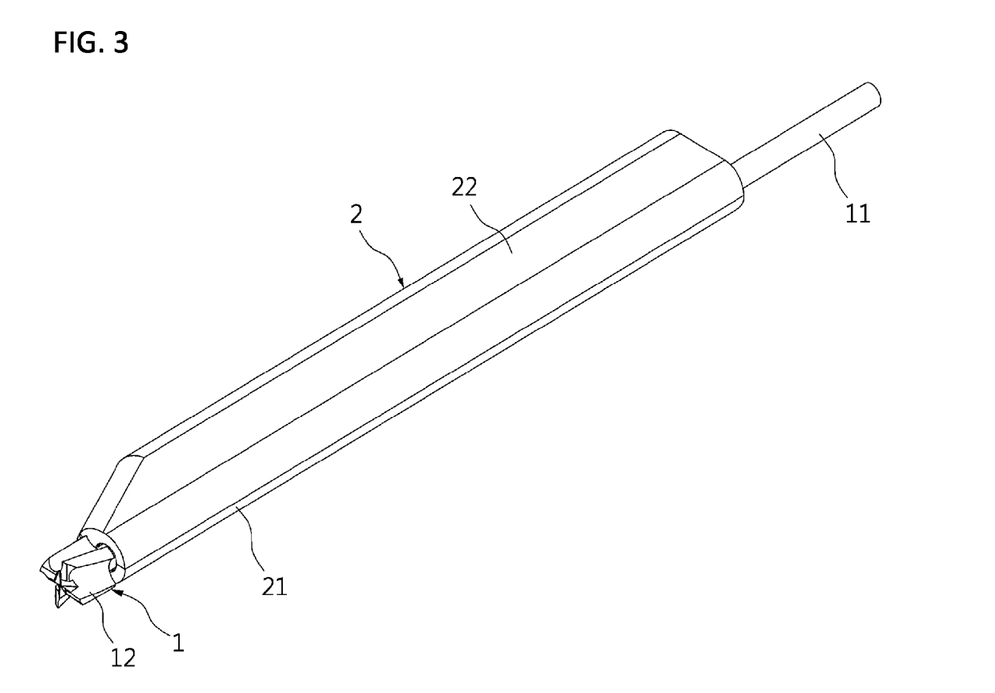
FIG. 3 is a perspective view of a cutting apparatus of a cutting system using a robot according to an embodiment of the present invention.
Figure 4:
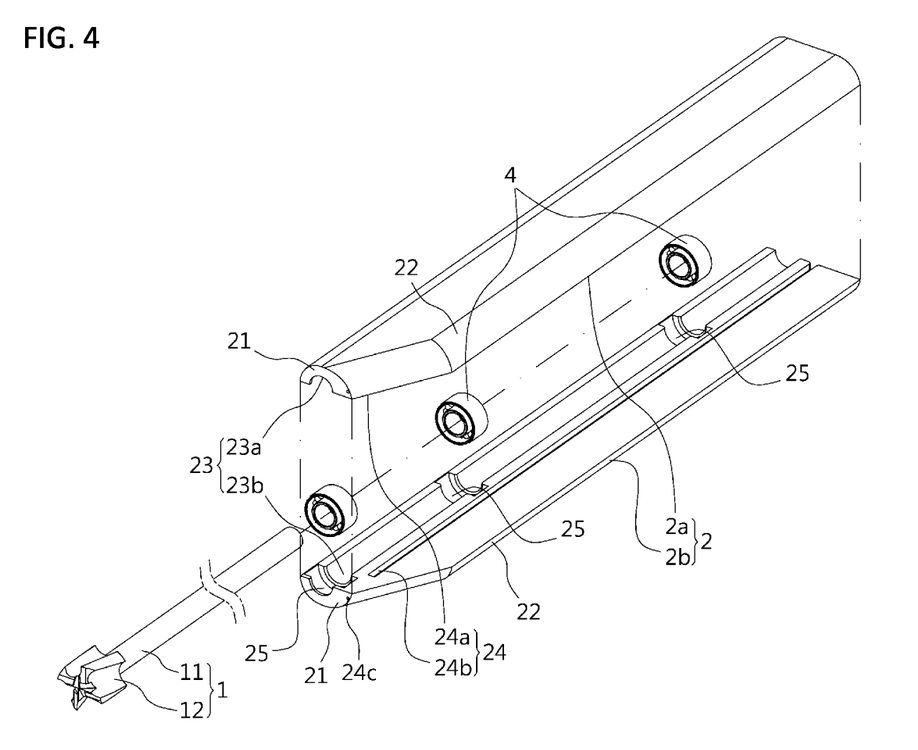
FIG. 4 is an exploded perspective view of a cutting apparatus of a cutting system using a robot according to an embodiment of the present invention.
Figure 5:
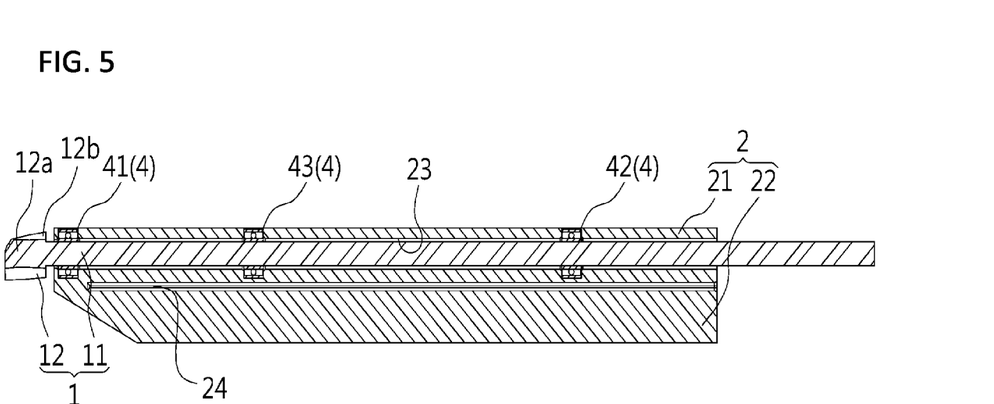
FIG. 5 is a cross sectional drawing of a cutting apparatus of a cutting system using a robot according to an embodiment of the present invention.

FIG. 3 is a perspective view of a cutting apparatus of a cutting system using a robot according to an embodiment of the present invention, FIG. 4 is an exploded perspective view of a cutting apparatus of a cutting system using a robot according to an embodiment of the present invention and FIG. 5 is a cross sectional drawing of a cutting apparatus of a cutting system using a robot according to an embodiment of the present invention.

Referring to FIGS. 3 to 5, a cutting apparatus of a cutting system using a robot according to an embodiment of the present invention is an apparatus to cut a bone, so as to operate on an implant (a) such as the knee joint, wherein the apparatus is provided in a robotic arm of a medical robot (not shown). The apparatus consists of a shaft 11 coupled to a motor provided in an arm of a robot (not shown); a cutter 1 equipped with a cutting head 12 at an end of the shaft 11; and a sleeve 2 which is provided with a shaft insertion hole formed to insert the shaft 11

The sleeve 2 is a component for rotatably supporting the shaft 11 comprising the cutter 12 and comprises a shaft insertion unit 21 and a reinforcing wing unit 22. Here, the major technical features of the present invention is that since the reinforcing wing unit 22 reinforces the rigidity against the bending of the shaft insertion unit 21, the shaft insertion unit 21 is not easily bent or deformed even with minimized thickness (outer diameter).

In addition, the sleeve 2 can be configured as a single member manufactured by a method of casting, forging, molding and so on. However, in this embodiment considering manufacturability and assembly performance, the sleeve 2 is assembled using bonding method such as welding after the symmetrical a upper sleeve 2a and a lower sleeve 2b are manufactured separately. To do this, the sleeve 2 is produced separately to a upper sleeve 2a and a lower sleeve 2b, and the upper sleeve 2a and the lower sleeve 2b comprise respectively a shaft groove 23a, 23b and a washing water groove 24a, 24b wherein the shaft groove 23a of the upper sleeve 2a and the shaft groove 23b of the lower sleeve 2b are connected to form the shaft insertion hole 23, and the washing water groove 24a of the upper sleeve s2 and the washing water groove 24b of the lower sleeve 2b are connected to form the washing water supply hole 24.

The shaft insertion unit 21 is formed as a vertical cross-sectional view having a rough "⊃" shape, and a shaft insertion hole 23 is formed along with a longitudinal direction of the shaft insertion unit 21 while penetrating inside the shaft insertion unit 21 wherein the shaft insertion hole 23 is inserted by the shaft 11. In addition, a bearing insertion groove 25 is formed in the shaft insertion hole 23 for inserting a support bearing 4 as will be described below. Here, the bearing insertion groove 25 is formed with such an inner diameter that $4.76^\Phi$ outer diameter of the support bearing 4 can be assembled in a tight fitting manner. And the shaft insertion unit 21 is formed so that the entire thickness of the shaft insertion unit 21 is about 0.5 mm to about 2 mm larger than the outer diameter of the support bearing 4.

In addition, a washing water supply hole 24 is formed along with the longitudinal direction of the shaft insertion unit 21. The washing water supply hole 24 is formed for the ejection of the washing water during operating a surgery of an artificial joint, etc., so that the washing water which is supplied from the washing water supply hole 24 is discharged through a jet 24a. Therefore, the washing water performs cleaning as well as cooling, thereby preventing the cutting surface from getting damaged due to excessive friction heat during cutting.

The reinforcing wing unit 22 is a component for reinforcing the rigidity against the bending generated from the load applied to the shaft insertion unit 21, and is formed to be extended integrally along with one side of the shaft insertion unit 21.

And the reinforcing wing unit 22 is formed with a structure of a rough rectangular plate shape, and is formed so that the width of the reinforcing wing unit 22 gets narrower toward the location of the cutter 2. In addition, it is more preferable that the reinforcing wing unit 22 is formed with the streamlined shape of getting narrower from inside to outside in width direction, in order to minimize the interference with the body tissue during cutting bone.

On the other hand, the shaft 11 is an axis with a round bar shape, and is rotatably supported by the support bearing 4 as will be described below. If the shaft 11 can cut bone while the shaft 11 not bending, there is no limit on a diameter of the shaft 11. But in an embodiment of the present invention, it is formed with a diameter of $2.36\Phi$, the minimum thickness of the sleeve 2.

And a cutting head 12 is formed to be divided into a plurality of blades 12b with the same angle interval, and the plurality of blades 12b protrudes on a head core 12a. In an embodiment of the present invention, the cutting head 12 is formed to have the range of −10% to +10% of 5.0 mm of an outer diameter.

Meanwhile, a plurality of support bearings 4 are installed to be inserted within the shaft insertion hole 23 of the shaft insertion unit 21 in order to support the shaft 11 rotatably. And the shaft insertion hole 23 includes a bearing groove 25 formed concavely for mounting the support bearing 4.

For example, the support bearing 4 as shown in FIGS. 4 and 5 consists of a first support bearing 41 installed in the front portion of the shaft insertion unit 21, a second support bearing 42 installed near the rear portion of the shaft insertion unit 21, and a third support bearing 43 installed with being closer to the first support bearing 41 between the first support bearing 41 and the second support bearing 42.

Here, considering that the shaft insertion unit 21 is thin, a high-speed ball bearing among many types of the support bearings 4 is installed, which is mainly used as a dental tool and is named as slip type high-speed ball bearing. However, the support bearings 4 produced by various manufacturers can be applied, for example the support bearings 4 which are produced by W&H company, KAYO company, NSK company and YOSHIDA company, and have 2.380 mm of the inner diameter and 4.763 mm of the outer diameter can be applied.

Figure 6:
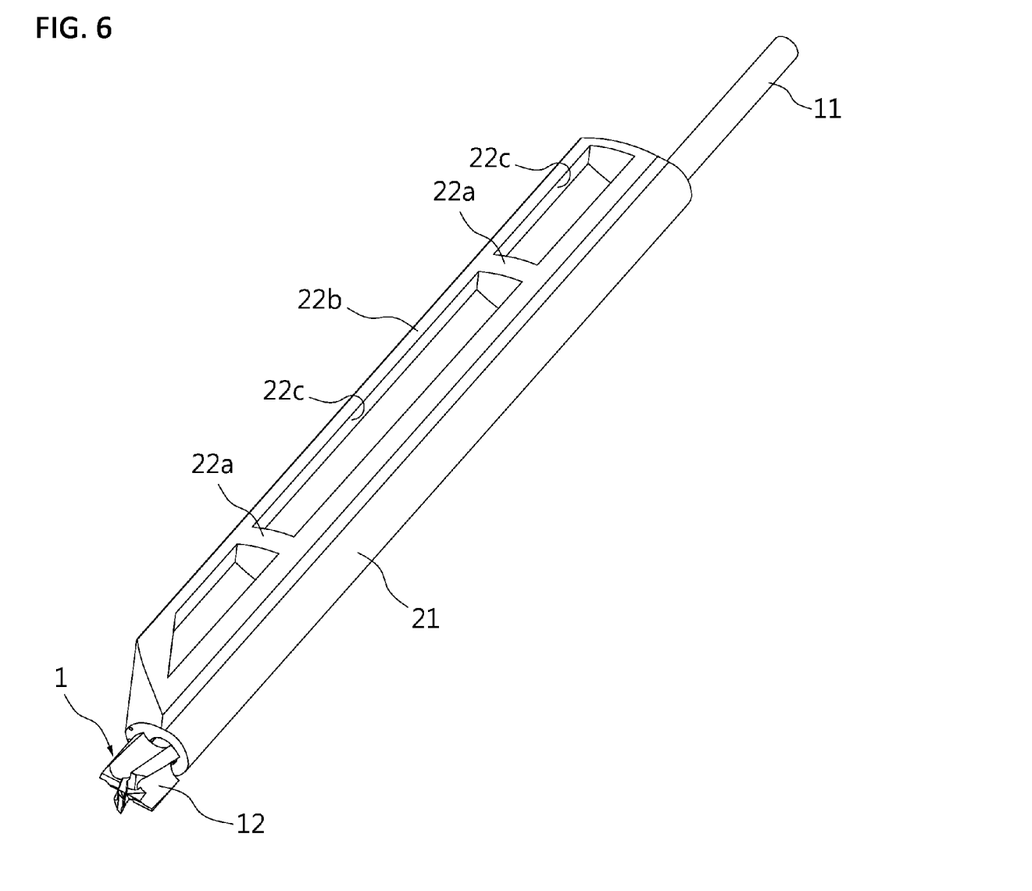
FIG. 6 is a perspective view of a cutting apparatus of a cutting system using a robot according to a modified embodiment of the present invention.

FIG. 6 is a perspective view of a cutting apparatus of a cutting system using a robot according to a modified embodiment of the present invention.

Referring FIG. 6, a cutting apparatus of a cutting system using a robot according to a modified embodiment of the present invention consists of a shaft 11, a cutter 1 equipped with a cutting head 12 at an end of the shaft 11, and a sleeve 2 including a shaft insertion unit 21 and a reinforcing wing unit 22, wherein for the simplicity of the structure, the reinforcing wing unit 22 includes a plurality of support sections 22a and a connecting section 22b, and hollow sections 22c are formed between the support section 22a and the connecting section 22b.

More specifically, the support sections 22a are formed to be connected to both ends of the shaft insertion unit and the portion inserted by the support bearing 4, because the load is concentrated on the both ends of the shaft insertion unit 21 when the shaft 11 rotates.

And, the connecting section 22b is string shaped and is formed to connect the ends of the support sections 22a.

As shown in FIG. 6, in a cutting apparatus of a cutting system using a robot according to a modified embodiment of the present invention, on operating the cutter 1, the area on which the load is concentrated due to the installation of the support bearing 4 is supported by the support section 22a. Therefore, the embodiment has advantage that the rigidity against the bending of the sleeve 2 is improved and the structure become simpler. As a result, because it is possible to reduce the weight of the cutting apparatus, the safety on operating can be improved and the convenience on procedure can be provided.

Hereinafter, operation of the cutting apparatus of the cutting system using the robot according to an embodiment of the present invention is briefly described.

First, in the cutter device according to the present invention configured as described above, if the cutter device is assembled and is coupled to the connecting section of the robotic arm, the shaft 11 of the cutter 1 is connected to receive power from the motor inserted into the connection section of the robotic art. (not shown)

Thus, after assembly of the cutter device is complete, the cutter device moves according to the operation of the robotic arm moving depending on the information input into the computer, and the cutting of a bone is performed while the cutter 1 rotates.

At this time, because the shaft 11 of the cutter 1 is supported by the first, the second and the third support bearings 41, 42, 43, even if the shaft 11 rotates at more than 60,000 rpm of rotational speed, stable rotational motion is performed without chattering.

In addition, when the cutter head 12 is cutting a knee bone (femur, tibia) with up-and-down motion, right-and-left motion and rotation motion, the heavy load is applied to the shaft 11. Therefore, the bending load is repeatedly applied to the shaft insertion section 21 of the sleeve 2. At this time, because the reinforcing wing unit 22 located on the longitudinal direction of the shaft insertion unit 11 supports the bending load applied to the shaft insertion unit 11, thereby reinforcing the rigidity against the bending so that the sleeve 2 cannot be easily bent or deformed even while minimizing the overall thickness of the sleeve 2. Accordingly, since it is possible to minimize the thickness of the sleeve 2, it is possible to prevent the interference and damage of the bone, muscle and the surrounding soft tissue on operation.

Hereinafter, another embodiment according to the present invention is described. However, a detailed description same or similar components as the embodiment described above will be skipped, and different components will be mainly described.

Figure 7:
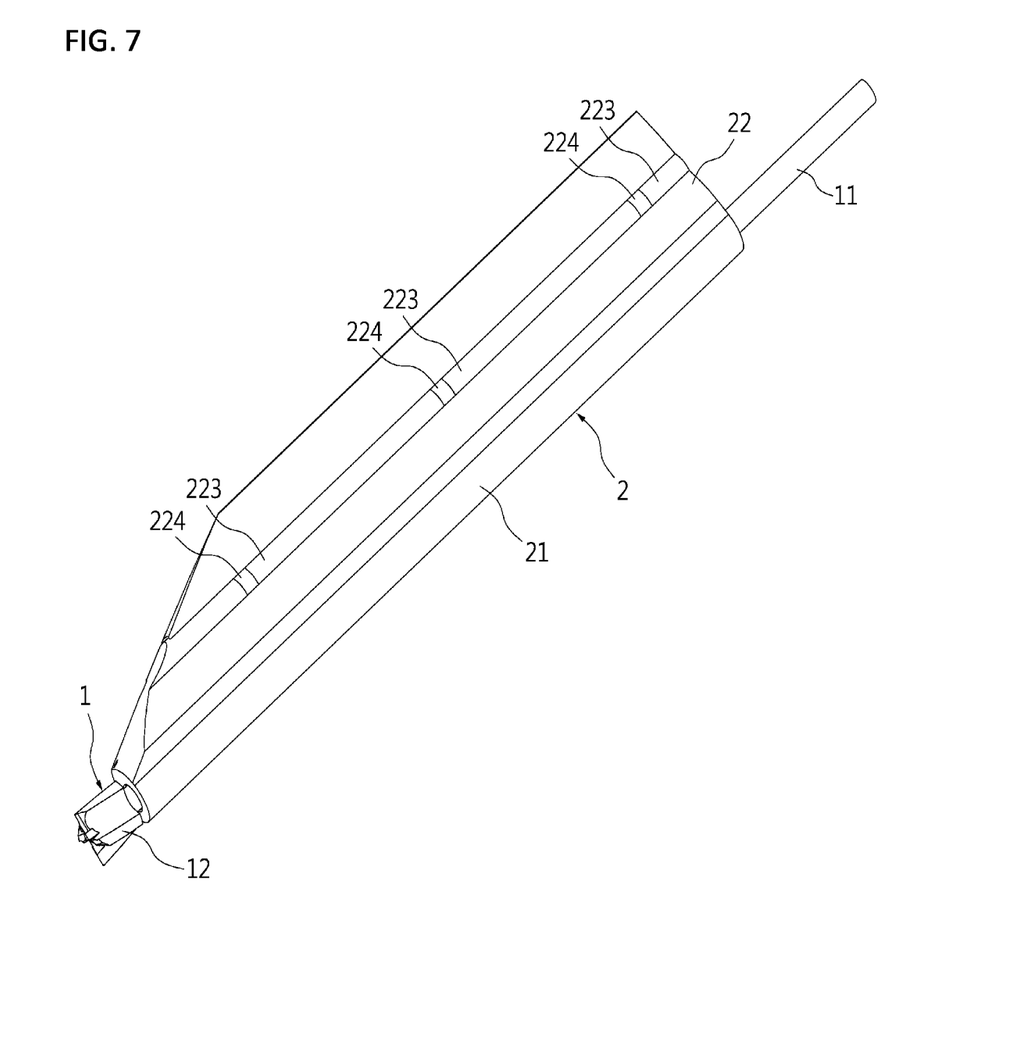
FIG. 7 is a perspective view of a cutting apparatus of a cutting system using a robot according to another embodiment of the present invention.
Figure 8:
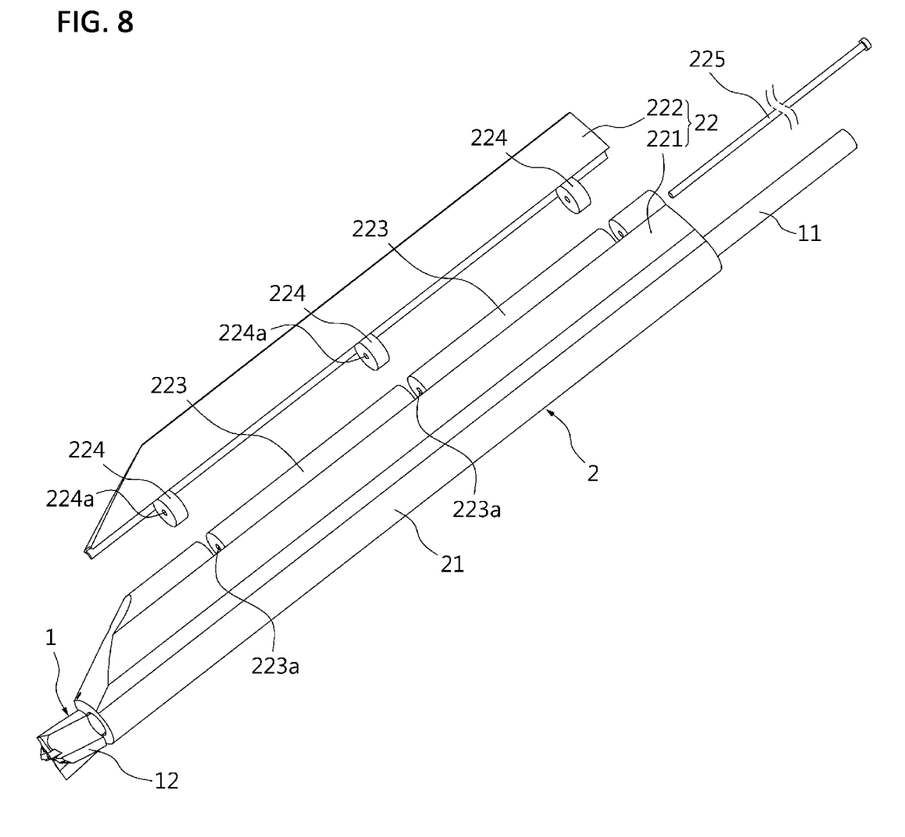
FIG. 8 is an exploded perspective view of a cutting apparatus of a cutting system using a robot according to an embodiment of the present invention.

FIG. 7 is a perspective view of a cutting apparatus of a cutting system using a robot according to another embodiment of the present invention, and FIG. 8 is an exploded perspective view of a cutting apparatus of a cutting system using a robot according to an embodiment of the present invention.

Referring FIGS. 7 and 8, a cutting apparatus of a cutting system using a robot according to another embodiment of the present invention consists of a shaft 11 coupled to a motor (not shown) provided in an arm of a robot, a cutter 1 equipped with a cutting head 12 at an end of the shaft 11, and a sleeve 2 into which the shaft 11 is inserted, wherein the sleeve 2 consists of a shaft insertion unit 21 which is provided with a shaft insertion hole formed to insert the shaft 11, and a reinforcing wing unit 22 formed to be extended integrally along with one side of the shaft insertion unit 21, wherein the reinforcing wing unit 22 is configured to move angularly along with the moving direction of the shaft insertion unit 21.

To do this, the reinforcing wing unit 22 consists of a fixed wing section 221 integrally connected to the shaft insertion unit 21, and a rotatable wing section 222 connected to the fixed wing section 221 and being rotatable.

More specifically, the fixed wing section 221 is extended into the shaft insertion unit 21, and a plurality of a first hinge section 223 are protruded parallel to the longitudinal direction of the shaft insertion unit 21 on the fixed wing section 221, wherein pin holes 223a penetrates through the first hinge section 223.

The rotatable wing section 222 has rectangular plate-like structure and is formed to get narrower toward the area of the cutting head 12 and a plurality of second hinge sections 224 are protruded on the bodies of the rotatable wing section 222, wherein the plurality of the second hinge sections 224 are coupled to the first hinge sections 223. In addition, the pin holes 224a penetrates the second hinge sections 224 in parallel with the longitudinal direction of the rotatable wing section 222 and the hinge pins 225 are inserted through the pin holes of the second hinge sections 224 to penetrate the pin holes of the first hinge section 223. As a result, the fixed wing section 22 and the rotatable wing section 222 are assembled.

According to the cutting device of the cutting system using the robot according to another embodiment of the present invention as described above, although the cutting head 12 moves on a curved or inclined surface when the cutting head 12 moves at up-and-down motion and right-and-left motion to cut a bone, the structure of the reinforcing wing section 222 with which the reinforcing wing section 222 can move angularly allows the cutting head 12 to move smoothly along with the moving direction of the shaft insertion unit 21. Therefore, it is possible not only to improve the safety and convenience of operation and reduce the time of operation, but also to minimize the interference and damage of a bone, muscle and the surrounding soft tissue on operating.

Although a few exemplary embodiments have been shown and described, it will be appreciated by those skilled in the art that changes may be made in these exemplary embodiments without departing from the principles and spirit of the invention, the scope of which is defined in the appended claims and their equivalents.

What is claimed is:

1. A cutting apparatus of a cutting system using a robot characterized in comprising:
    a shaft coupled to a motor provided in an arm of a robot;
    a cutter equipped with a cutting head at an end of the shaft;
    a sleeve into which the shaft is inserted;
    wherein, the sleeve comprises:
        a shaft insertion unit which is provided with a shaft insertion hole formed to insert the shaft;
        a reinforcing wing unit formed to be extended integrally along with one side of the shaft insertion unit, thereby reinforcing rigidity against the bending of the shaft insertion unit; and
    wherein the reinforcing wing unit comprises:
        a fixed wing section integrally connected to the shaft insertion unit and being rotatable; and
        a rotatable wing section connected to the fixed wing section and being rotatable.

2. The cutting apparatus according to claim 1, further comprising a plurality of support bearings installed inside the shaft insertion hole in order to support the shaft rotatably.

3. The cutting apparatus according to claim 2, wherein
    the reinforcing wing unit consists of support sections connected to end regions of the shaft insertion unit and regions into which the support bearings are inserted, and connecting sections for connecting the support sections,
    wherein hollow sections are formed between the support sections and the connecting sections.

4. The cutting apparatus according to claim 1, characterized in comprising:
    a plurality of first hinge sections which are installed on the fixed wing section and having pinholes perforating on the first hinge sections;
    a plurality of second hinge sections which are installed on the rotatable wing section in order to be connected to the first hinge sections and having pinholes perforating on the second hinge sections; and
    hinge pins inserted into the pinholes of the first hinge sections and the second hinge sections.

5. The cutting apparatus according to claim 1,
    wherein the sleeve is produced separately to a upper sleeve and a lower sleeve and then is assembled, and the upper sleeve and the lower sleeve comprise respectively a shaft groove and a washing water groove, wherein the shaft groove of the upper sleeve and the shaft groove of the lower sleeve are connected to form the shaft insertion hole, and the washing water groove of the upper sleeve and the washing water groove of the lower sleeve are connected to form a washing water supply hole.

6. The cutting apparatus according to claim 2, wherein the sleeve is produced separately to a upper sleeve and a lower sleeve and then is assembled, and the upper sleeve and the lower sleeve comprise respectively a shaft groove and a washing water groove, wherein the shaft groove of the upper sleeve and the shaft groove of the lower sleeve are connected to form the shaft insertion hole, and the washing water groove of the upper sleeve and the washing water groove of the lower sleeve are connected to form a washing water supply hole.

7. The cutting apparatus according to claim 3, wherein the sleeve is produced separately to a upper sleeve and a lower sleeve and then is assembled, and the upper sleeve and the lower sleeve comprise respectively a shaft groove and a washing water groove, wherein the shaft groove of the upper sleeve and the shaft groove of the lower sleeve are connected to form the shaft insertion hole, and the washing water groove of the upper sleeve and the washing water groove of the lower sleeve are connected to form a washing water supply hole.

8. The cutting apparatus according to claim 4, wherein the sleeve is produced separately to a upper sleeve and a lower sleeve and then is assembled, and the upper sleeve and the lower sleeve comprise respectively a shaft groove and a washing water groove, wherein the shaft groove of the upper sleeve and the shaft groove of the lower sleeve are connected to form the shaft insertion hole, and the washing water groove of the upper sleeve and the washing water groove of the lower sleeve are connected to form a washing water supply hole.

* * * * *